(12) United States Patent
Sanger et al.

(10) Patent No.: US 6,750,195 B2
(45) Date of Patent: Jun. 15, 2004

(54) USE OF 5-HT4 MODULATORS FOR THE MANUFACTURE OF A MEDICAMENT FOR THE TREATMENT OF THE BLADDER DISEASES

(75) Inventors: Gareth John Sanger, Harlow (GB); Kay Alison Wardle, Harlow (GB)

(73) Assignee: SmithKline Beecham Corporation p.l.c., Brentford (GB)

( * ) Notice: Subject to any disclaimer, the term of this patent is extended or adjusted under 35 U.S.C. 154(b) by 0 days.

(21) Appl. No.: 10/260,323

(22) Filed: Sep. 27, 2002

(65) Prior Publication Data

US 2003/0045452 A1 Mar. 6, 2003

Related U.S. Application Data

(63) Continuation of application No. 09/969,408, filed on Oct. 2, 2001, now abandoned, which is a continuation of application No. 09/710,733, filed on Nov. 9, 2000, now abandoned, which is a continuation of application No. 08/959,642, filed on Oct. 28, 1997, now abandoned, which is a continuation of application No. 08/576,261, filed on Dec. 21, 1995, now abandoned, which is a continuation of application No. 08/256,027, filed as application No. PCT/GB92/02376 on Dec. 21, 1992, now abandoned.

(51) Int. Cl.[7] ............... A61K 31/00; A61K 31/215; A61K 31/435; A61K 31/44; A61K 31/445

(52) U.S. Cl. .................. 514/1; 514/1; 514/183; 514/506; 514/304; 514/327; 514/331; 514/529

(58) Field of Search .................. 514/210, 1, 183, 514/277, 279, 299, 315, 317, 304, 327, 331, 529

(56) References Cited

U.S. PATENT DOCUMENTS

| | | | |
|---|---|---|---|
| 5,318,977 A | | 6/1994 | Becker et al. |
| 5,362,756 A | | 11/1994 | Riviere et al. |
| 5,492,919 A | * | 2/1996 | Sanger et al. ............ 514/323 |
| 5,580,885 A | | 12/1996 | King et al. |

FOREIGN PATENT DOCUMENTS

| | | |
|---|---|---|
| EP | 0 467 365 A2 | 1/1992 |
| EP | 0 501 322 A1 | 9/1992 |
| FR | 76530 | 9/1961 |
| WO | WO 91/16045 | 10/1991 |
| WO | WO 92/14727 A1 | 9/1992 |
| WO | WO 93/02677 A1 | 2/1993 |
| WO | WO 93/03725 A1 | 3/1993 |
| WO | WO 93/05038 A1 | 3/1993 |
| WO | WO 93/05040 A1 | 3/1993 |
| WO | WO 93/08187 A1 | 4/1993 |

OTHER PUBLICATIONS

Etienne, M.; Verlinden, M.; Brassinne, M.; "Treatment with Cisapride of the Gastrointestinal and Urological Sequelae of Spinal Cord Transection: Case Report", Paraplegia, 26 (1998), pp 162–164.*

A.P.C.W. Ford and M.S.Kava, Chapter 8: "5–HT4 receptors in lower urinary tract tissues", pp. 171–193, in: "5–HT4 receptors in the Brain and the Periphery", ed. R.M. Englen, Springer–Verlag and RG Landes & Co, 1998.
M.V. Waikar, APDW Ford et al., Br. J. Pharmacol., 1994, 111(1), 213–218.
R.M. Eglen et al., Br. J. Pharmacol., vol. 107, Dec. 1992 Proceedings Supplement, 439P.
J. Bermudez et al., J. Med. Chem., 1990, 33, 1924–1929.
K.H. Buchheit and R. Gamse, Naunyn–Schmiedeberg's Arch. Pharmacol., 1991, 343 (Suppl.), R101.
K.H. Buchheit, R. Gamse et al., Eur. J. Pharmacol., 1991, 200, 373–374.
ML Cohen et al., J. Pharmacol. Exptl. Therap., 1989, 248, 197–201.
M. Corsi et al., Br. J. Pharmacol., 1991, 104, 709.
D.A. Craig et al., J. Pharmacol. Exp. Therapeutics, 1990, 252(3), 1378–1386.
G.H. De Groot, et al., Paraplegia, vol. 26, No. 3, 1988, pp. 159–161.
A. Dumuis et al., Eur. J. Pharmacol., 1988, 146, 187–188.
A. Dumuis et al., Naunyn–Schmiedeberg's Arch. Pharmacol., 1989, 340, 403–410.
A. Dumuis et al., Naunyn–Schmiedeberg's Arch. Pharmacol., 1992, 345, 264–269.
C.J. Elswood et al., Eur. J. Pharmacol., 1991, 196, 149–155.
M. Etienne, et al., Paraplegia, vol. 26, No. 3, 1988, pp. 162–164.
A.P.C.W. Ford et al., "5HT4 receptor agonism inhibits neuronally–mediated responses in monkey urinary bladder", 2nd International Symposium on Serotonin, Houston, Sep. 1992, p. 53.
R. Gamse, Cancer Treatment Reviews, 1990, 17, 301–305.
P. Hanson, et al., Acta Belg. Med. Phys., vol. 12, No. 3, 1989, pp. 81–88.
J.R. Hindmarsh et al., Br. J. Pharmacol., 1977, 61, 115P.
A.J. Kaumann, Naunyn–Schmiedeberg's Arch. Pharmacol., 1990, 342, 619–622.
A.J. Kaumann et al., Br. J. Pharmacol., 1990, 100, 879–885.
M. Lazzaroni, et al., Digestion 37: 110–113 (1987).
E. Messori, et al., Br. J. Pharmacol. 115, 677–683 (1995).
DR Nelson et al. Biochem. Pharmacol., 1989, 38(10), 1693–1695.

(List continued on next page.)

Primary Examiner—Gollumudi S. Kishore
Assistant Examiner—Simon J. Oh
(74) Attorney, Agent, or Firm—Soma G. Simon; Mary E. McCarthy; Charles M. Kinzig

(57) ABSTRACT

A compound which acts as an antagonist at 5-$HT_4$ receptors is of potential use in the treatment of conditions associated with bladder hypersensitivity, such as urinary incontinence, which is often associated with irritable bowel syndrome (IBS) and a compound which acts as an agonist at 5-$HT_4$ receptors is of potential use in the treatment of conditions associated with a poorly functioning bladder, such as urinary bladder hypoactivity following prostectomy.

6 Claims, No Drawings

OTHER PUBLICATIONS

William D. Steers, et al. *Drug Dev. Res.* vol. 27, No. 4, 1992, pp. 361–375.
GJ Sanger and DR Nelson, *Eur. J. Pharmacol.*, 1989, 159, 113–124.
M. Tonini, et al. *Br. J. Pharmacol.*, 1994, 113, 1–2.
M. Turconi, et al., *Drugs of the Future*, vol. 16, No. 11, 1991, pp. 1011–1026.

JW Upward et al., *Eur. J. Cancer*, 1990, 26 (Suppl.), S12–S15.
S. Vaidyanathan, *J. Urology*, 1981, vol. 125 42–43.
H van den Brink et al, *Eur. J. Pharmacol.*, 1990, 181(1–2), 119–125; (Chem Abs 1990, vol 113, p57, abstract 126402c).
*Scand. J. Urology and Nephrology*, 1979, 13, 79–82.

* cited by examiner

USE OF 5-HT4 MODULATORS FOR THE MANUFACTURE OF A MEDICAMENT FOR THE TREATMENT OF THE BLADDER DISEASES

This application is a continuation of application Ser. No. 09/969,408 filed Oct. 2, 2001, now abandoned which is a continuation of application Ser. No. 09/710,733, filed Nov. 9, 2000, now abandoned, which is a continuation of application Ser. No. 08/959,642, filed Oct. 28, 1997, now abandoned, which is a continuation of application Ser. No. 08/576,261, filed Dec. 21, 1995, now abandoned, which is a continuation of application Ser. No. 08/256,027, filed Jun. 21, 1994, now abandoned, which is a 371 national stage of PCT/GB92/02376 filed Dec. 21, 1992, which claims priority from Great Britain application numbers GB 9127184.1, filed Dec. 21, 1991, GB 9127185.8, filed Dec. 21, 1991, and GB 9219354.9 filed Sep. 12, 1992.

This invention relates to treatment of conditions associated with bladder hypersensitivity, and conditions associated with a poorly functioning bladder.

European Journal of Pharmacology 146 (1988), 187–188, and Naunyn-Schmiedeberg's Arch. Pharmacol. (1989) 340:403–410, describe a non classical 5-hydroxytryptamine receptor, now designated the $5\text{-}HT_4$ receptor, and that tropisetron (ICS 205–930), which is also a $5\text{-}HT_3$ receptor antagonist, acts as an antagonist at this receptor and metoclopramide is an agonist at this receptor.

WO 91/16045 (SmithKline and French Laboratories Limited) describes the use of cardiac $5\text{-}HT_4$ receptor antagonists in the treatment of atrial arrhythmias and stroke.

Metoclopramide has been shown to be effective in treating a poorly functioning bladder, (Scand. J. Urology and Nephrology, 13:79–82 (1979) but this has not been specifically linked to any known action of metoclopramide.

There are reports in the literature of $5\text{-}HT_4$ receptors potentiating contractions in human bladder (Br. J. Pharmacol, 61, 115P) and inhibiting contractions in monkey bladder (2nd International Symposium on Serotonin, Houston, September 1992, page 86).

We have now discovered that a compound which acts as an antagonist at $5\text{-}HT_4$ receptors is of potential use in the treatment of conditions associated with bladder hypersensitivity, such as urinary incontinence, which is often associated with irritable bowel syndrome (IBS) and a compound which acts as an agonist at $5\text{-}HT_4$ receptors is of potential use in the treatment of conditions associated with a poorly functioning bladder, such as urinary bladder hypoactivity following prostectomy. When used herein the term '$5\text{-}HT_4$ modulator' is used to denote antagonists and agonists.

The invention therefore provides a method for the treatment and/or prophylaxis of conditions associated with bladder hypersensitivity and conditions associated with a poorly functioning bladder in mammals, including humans, which method comprises administering to the mammal in need of such treatment and/or prophylaxis, an effective and/or prophylactic amount of a $5\text{-}HT_4$ modulator.

$5\text{-}HT_4$ modulators may be identified according to standard methods, such as those described hereinafter, and that described in Naunyn-Schmiedeberg's Arch Pharmacol. 342, 619–622.

Examples of $5\text{-}HT_4$ receptor antagonists include ICS 205–930 (tropisetron—Sandoz), R 50 595 (Janssen), which is described in FR 76530 and Eur. J. Pharmacol., 181 119–125 (1990), and SDZ 205–557, which is described by K. H. Buchheit and R. Gamse in Naunyn-Schmiedeberg's Arch. Pharmacol., 343 (Suppl.), R101 (1991). DAU 6285 (Naunyn-Schmiedeberg's Arch. Pharmacol, 345; 264–269 (1992) and RS 23597-190 (Syntex—British Pharmacology Society Meeting, September 1992).

EP-A-501322 (Glaxo Group Limited) describes indole derivatives having $5\text{-}HT_4$ receptor antagonist activity and reports $5\text{-}HT_4$ receptors are believed to be associated with conditions involving inter alia the urinary tract (e.g. urinary incontinence).

Examples of $5\text{-}HT_4$ receptor agonists include cisapride, renzapride and zacopride.

In one aspect, the $5\text{-}HT_4$ modulator is more potent at $5\text{-}HT_4$ receptors than at $5\text{-}HT_3$ receptors.

Preferably, the $5\text{-}HT_4$ modulator is in substantially pure pharmaceutically acceptable form.

The administration of the $5\text{-}HT_4$ modulator may be by way of oral, sublingual, transdermal or parenteral administration.

An amount effective to treat the disorder hereinbefore described depends on the usual factors such as the nature and severity of the disorder being treated and the weight of the mammal. However, a unit dose will normally contain 0.1 to 50 mg for example 0.5 to 10 mg, of the $5\text{-}HT_4$ modulator. Unit doses will normally be administered once or more than once a day, for example 2, 3, or 4 times a day, more usually 1 to 3 times a day, such that the total daily dose is normally in the range, for a 70 kg adult of 0.1 to 50 mg, for example 0.1 to 5 mg, that is in the range of approximately 0.001 to 1 mg/kg/day, more usually 0.005 to 0.2 mg/kg/day.

For oral or parenteral administration, it is greatly preferred that the $5\text{-}HT_4$ modulator is administered in the form of a unit-dose composition, such as a unit dose oral or parenteral composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling or tabletting. Repeated blending operations may be used to distribute the active agent throughout those compositions employing large quantities of fillers. Such operations are, of course, conventional in the art.

Oral liquid preparations may be the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the 5-HT$_4$ modulator and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the treatment concerned.

The present invention also provides the use of a 5-HT$_4$ modulator in the manufacture of a medicament for use in the treatment and/or prophylaxis of conditions associated with a poorly functioning bladder and bladder hypersensitivity. Such treatment and/or prophylaxis may be carried out as hereinbefore described.

The present invention further provides a pharmaceutical composition for use in the treatment and/or prophylaxis of conditions associated with a poorly functioning bladder and bladder hypersensitivity, which comprises a 5-HT$_4$ modulator, and a pharmaceutically acceptable carrier. Such compositions may be prepared in the manner as hereinbefore described.

5-HT$_4$ Modulator Activity
1) Guinea Pig Colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% $CO_2$ in $O_2$ and maintained at 37° C. In all experiments, the Krebs solution also contains methiothepin $10^{-7}$ Mn and granisetron $10^{-6}$M to block effects at 5-HT$_1$, 5-HT$_2$ and 5-HT$_3$ receptors.

After construction of a simple concentration-response curve with 5-HT, using 30 s contact times and a 15 min dosing cycle, a concentration of 5-HT is selected so as to obtain a contraction of the muscle approximately 40–70% maximum (10–9M approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-HT$_4$ modulator are then added to the bathing solution. The effects of this compound are then determined as a percentage reduction of the contractions evoked by 5-HT or by DMPP.

From this data, IC$_{50}$ values are determined, being defined as the concentration of antagonist or agonist which reduces or increases the contraction by 50%. A compound which reduces the response to 5-HT but not to DMPP is believed to act as a 5-HT$_4$ receptor antagonist and a compound which increases the response to 5-HT but not to DMPP is believed to act as a 5-HT$_4$ receptor agonist.

2) Rat Oesophagus

Rat oesophageal tunica muscularis mucosae is set up according to Baxter et. al. Naunyn-Schmiedeberg's Arch. Pharmacol., 343, 439–446 (1991). The inner smooth muscle tube of the muscularis mucosae is isolated and mounted for isometric tension recording in oxygenated (95% $O_2$/5% $CO_2$) Tyrodes solution at 37° C. All experiments are performed in pargyline pre-treated preparations (100 μM for 15 min followed by washout) and in the presence of cocaine (30 μM). Relaxant responses to 5-HT are obtained after pre-contracting the oesophagus tissue with carbachol (3 μM).

What is claimed is:

1. A method for the treatment of a condition associated with bladder hypersensitivity, said condition being urinary incontinence in mammals, including humans, which method comprises administering to the mammal in need of such treatment, an effective amount of a 5-HT$_4$ receptor antagonist.

2. A method according to claim 1 which is for the treatment of urinary incontinence associated with irritable bowel syndrome.

3. A method according to claim 1, wherein the 5-HT$_4$ receptor antagonist is:

(i)

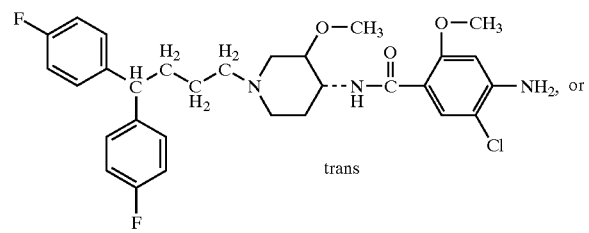

(ii) 2-methoxy-4-amino-5-chloro-benzoic acid 2-(diethylamino) ethyl ester, or (iii)

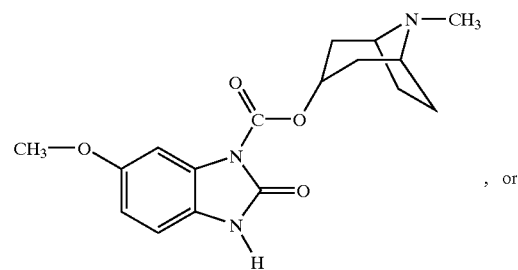

, or (iv) 3-(piperidin-1-yl)propyl 4-amino-5-chloro-2-methoxybenzoate hydrochloride.

4. A method as claimed in claim 1, wherein the 5-HT$_4$ receptor antagonist is more potent at 5-HT$_4$ receptors than at 5-HT$_3$ receptors.

5. A method as claimed in claim 1, wherein the mammals are humans.

6. A method as claimed in claim 4, wherein the mammals are humans.

* * * * *

UNITED STATES PATENT AND TRADEMARK OFFICE
CERTIFICATE OF CORRECTION

PATENT NO. : 6,750,195 B2
DATED : June 15, 2004
INVENTOR(S) : Sanger et al.

It is certified that error appears in the above-identified patent and that said Letters Patent is hereby corrected as shown below:

Title page,
Item [73], Assignee, should read -- SmithKline Beecham p.l.c. --
Insert Item:
-- [30]    Foreign Application Priority Data

| | | |
|---|---|---|
| December 21, 1991 | (GB) | 9127184.1 |
| December 21, 1991 | (GB) | 9127185.8 |
| September 12, 1992 | (GB) | 9219354.9 -- |

Signed and Sealed this

Fourteenth Day of December, 2004

JON W. DUDAS
*Director of the United States Patent and Trademark Office*